United States Patent [19]

Tesio

[11] Patent Number: 5,776,111
[45] Date of Patent: Jul. 7, 1998

[54] MULTIPLE CATHETER ASSEMBLY

[75] Inventor: Franco Tesio, Pordenone, Italy

[73] Assignee: Medical Components, Inc., Harleysville, Pa.

[21] Appl. No.: 746,260

[22] Filed: Nov. 7, 1996

[51] Int. Cl.[6] ............................................. A61M 5/00
[52] U.S. Cl. .................... 604/264; 604/174; 604/280; 604/29
[58] Field of Search .................... 604/19, 27, 39, 604/43, 93, 94, 173, 174, 175, 179, 180, 264, 265, 280, 283, 284, 905; 128/656–658

[56] References Cited

U.S. PATENT DOCUMENTS

| | | |
|---|---|---|
| 3,359,974 | 12/1967 | Khalil . |
| 3,719,737 | 3/1973 | Vaillancourt et al. . |
| 3,804,097 | 4/1974 | Rudie . |
| 3,935,857 | 2/1976 | Co . |
| 4,050,667 | 9/1977 | Kossett . |
| 4,072,146 | 2/1978 | Howes . |
| 4,385,631 | 5/1983 | Uthmann . |
| 4,397,647 | 8/1983 | Gordon . |
| 4,402,683 | 9/1983 | Kapman ............................ 604/175 |
| 4,405,313 | 9/1983 | Sisley et al. . |
| 4,435,174 | 3/1984 | Redmond et al. . |
| 4,516,968 | 5/1985 | Marshall et al. . |
| 4,632,670 | 12/1986 | Mueller, Jr. . |
| 4,645,492 | 2/1987 | Weeks . |
| 4,650,474 | 3/1987 | De Backer . |
| 4,654,032 | 3/1987 | Morales-George . |
| 4,687,471 | 8/1987 | Twardowski et al. ............. 604/175 |
| 4,699,616 | 10/1987 | Nowak et al. . |
| 4,895,561 | 1/1990 | Makurkar . |
| 4,981,475 | 1/1991 | Haindl . |
| 5,053,003 | 10/1991 | Dadson et al. . |
| 5,059,170 | 10/1991 | Cameron ............................ 604/280 |
| 5,084,013 | 1/1992 | Takase ............................ 604/43 |
| 5,107,856 | 4/1992 | Kristiansen et al. . |
| 5,156,592 | 10/1992 | Martin et al. . |
| 5,171,216 | 12/1992 | Dasse et al. . |
| 5,209,723 | 5/1993 | Twardowski et al. . |
| 5,215,531 | 6/1993 | Maxson et al. . |
| 5,224,935 | 7/1993 | Hollands . |
| 5,267,970 | 12/1993 | Chin et al. . |
| 5,346,471 | 9/1994 | Raulerson . |
| 5,350,358 | 9/1994 | Martin ............................ 604/280 |
| 5,378,241 | 1/1995 | Haindl ............................ 604/264 |
| 5,435,306 | 7/1995 | Stuart . |
| 5,498,248 | 3/1996 | Milder ............................ 604/280 |
| 5,520,664 | 5/1996 | Bricault, Jr. et al. ............ 604/280 |
| 5,562,618 | 10/1996 | Cai et al. ........................ 604/93 |

OTHER PUBLICATIONS

Brochure entitled "The MedComp TESIO Catheter," MedComp, Harleysville, PA, date unknown, 4 pages.

B. Canaud et al., "Internal Jugular Vein Cannulation with Two Silicone Rubber Catheters: A New and Safe Temporary Vascular Access for Hemodiaylsis," *Artificial Organs*, 1986; 10(5); 397–403.

F. Tesio et al., "Double Catheterization of the Internal Jugular Vein for Hemodialysis: Indications, Techniques, and Clinical Results," *Artificial Organs*, 1994; 18(4): 301–304.

*Primary Examiner*—Michael Buiz
*Assistant Examiner*—Jennifer R. Sadula
*Attorney, Agent, or Firm*—Panitch Schwarze Jacobs & Nadel, P.C.

[57] ABSTRACT

A double catheter assembly is provided which includes two single lumen catheters that pass through the center portion of a stabilizer disk in a juxtaposed relationship. The stabilizer disk may be provided with holes in its periphery that facilitate suturing of the disk to a patient's skin at the insertion site, once the catheter is implanted. The portions of the catheters that are external to the insertion point are characterized by having a permanent bend proximate to the stabilizer disk that promotes patient compliance when the double catheter assembly is used in a catheterization.

16 Claims, 2 Drawing Sheets

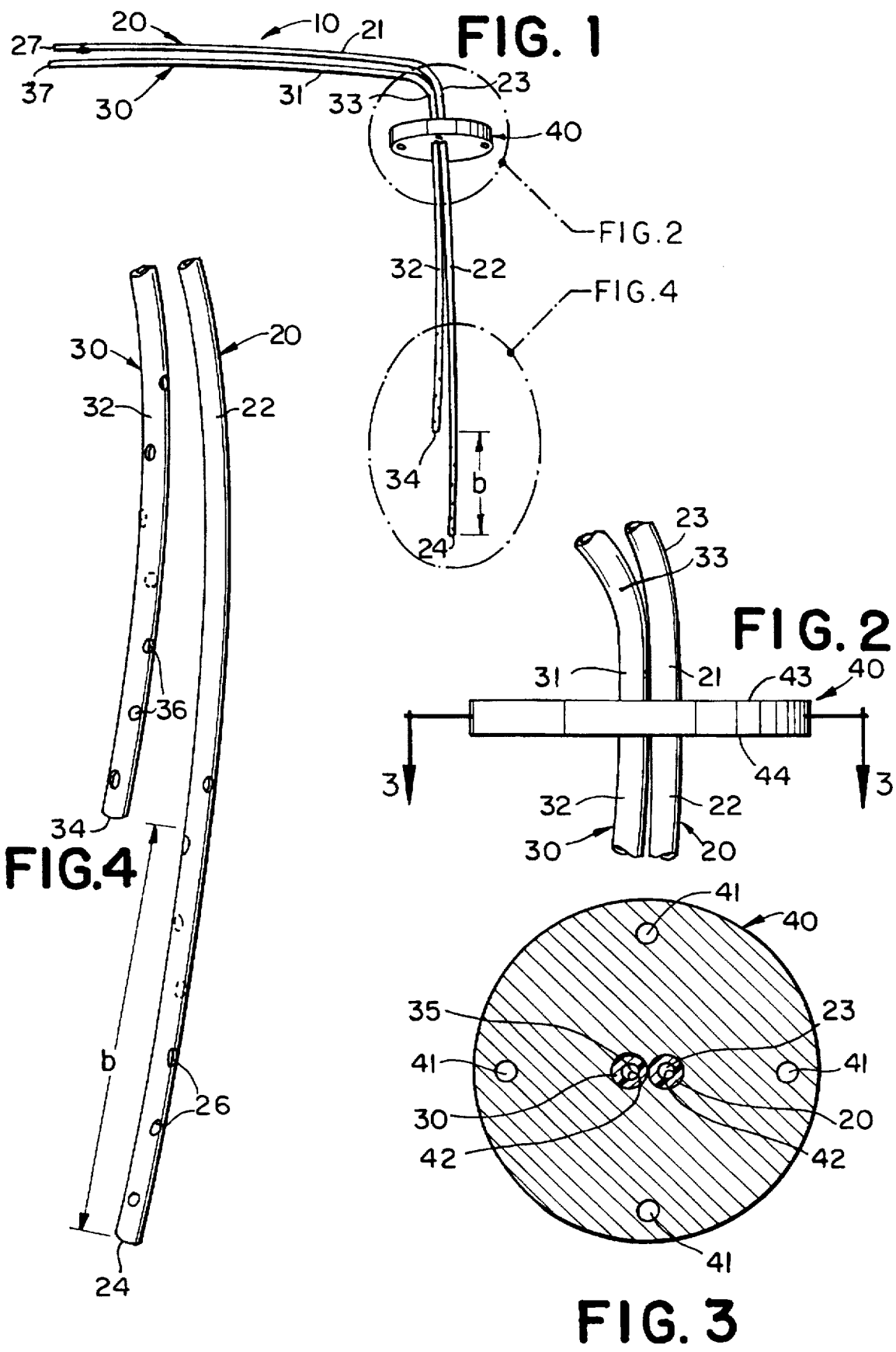

MULTIPLE CATHETER ASSEMBLY

BACKGROUND OF THE INVENTION

The present invention relates to a multiple catheter assembly which is useful for providing vascular access. Catheters are typically tubular instruments used in medical procedures in which a portion of the catheter is inserted into a venous location or other cavity in the body for introduction or removal of fluids. Catheterization may be long term, where the implanted catheter is used in the treatment of a chronic condition, for example, in continuous or periodic medical treatment procedures extending over several days, weeks or longer. Short-term catheterization may be used for the same purposes as long-term catheterizations, for example, for hemodialysis, but are typically used for treatment of acute conditions, for example, in emergency situations. In such cases, the catheterization procedure must be completed expeditiously and within a short time frame. Catheter designs and catheterization techniques commonly employed in long-term catheterization are generally inappropriate for short-term catheterizations. For example, long-term catheterizations often employ surgical procedures, such as tunnelization of the catheter under the epidermis as a means for stabilizing the catheter, or utilize catheters with complex designs intended for semipermanent or long-term implantation in the patient.

Catheterizations for the introduction or removal of fluids may be performed by using various types of catheters. A single catheter having multiple lumens is one category, a typical example of a multiple lumen catheter being a dual lumen catheter in which one lumen in the catheter tube introduces fluids and the other lumen in the tube removes fluids. Catheterization may also be performed by using two or more separate, individual catheters, each with a single lumen, inserted through one or more incisions into an area to be catheterized. One such multiple catheter assembly is known as a Tesio catheter.

A multiple catheter assembly using two, single-lumen catheters has several advantages for applications of use such as infusion, perfusion, hemodialysis and the like. The Tesio catheter which has two, single-lumen catheters provides excellent flow conditions due to the large, circular cross-section of each of the individual lumens. This is advantageous with newer dialysis machines which are designed to be operated at high processing rates that decrease the length of the patient's treatment time but that increase the incidence of flow problems with some smaller lumen diameter catheters. With a Tesio catheter, catheter closure or blockage, and recirculation or vessel wall trauma are minimized because the lumens extend through separate catheters and their distal end openings are not generally as close together as are the distal end openings of some unitary multiple lumen catheters. Further the distal ends of each catheter can move independent of each other within the same, or a different, vessel. In addition, multiple apertures can be provided to both the intake and return catheters extending through the catheter walls over the full 360° of the periphery of each catheter in the system since the device is not unitary.

Generally, to insert a catheter in a target blood vessel, the vessel is located and identified by aspiration with a long hollow needle in accordance with the well-known Seldinger technique. When blood enters a syringe attached to the needle, the syringe is disconnected and a thin guide wire is passed through the needle into the hollow passage, or lumen, of the vessel. The needle is then removed leaving one end of the guide wire within the vessel and the other end projecting beyond the surface of the skin.

At this point, several options are available to a physician for catheter placement. The simplest is to pass a catheter into the vessel directly over a guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole. The catheter is then passed over the guide wire, and the guide wire and dilator removed.

For insertion of multiple catheter assemblies, such as a Tesio catheter which may lack sufficient rigidity, a physician may use an introducer sheath to insert (place) the catheter. A Tesio catheter is a double catheter assembly in which two individual single-lumen catheters are inserted typically in two different locations for removing and introducing fluids to an area of the body to be catheterized. For example, the catheters may be used for hemodialysis by inserting each catheter in the same vein at two different locations of the vein, such as the internal jugular vein, or by inserting each catheter in two separate veins, such as the femoral veins. The introducer sheath is simply a large, stiff thin-walled tube which serves as a temporary conduit for the catheter which is being inserted into the desired location. The introducer sheath is positioned by placing a dilator device inside of the introducer and passing both the dilator and the introducer together into the vessel. The guide wire left in the vessel after insertion by syringe (as described above) and the dilator are then removed, leaving the thin-walled introducer sheath in place. The catheter is then passed through the introducer sheath and into the vessel. The sheath is typically removed over the catheter once the catheter is properly positioned in the correct location.

Once the catheter is in place, the catheter must be stabilized or anchored to secure the portion of the catheter extending proximal to the catheterized area so that there is no displacement of the distal portion of the catheter positioned in the area to be catheterized.

Typical anchoring devices for catheters intended for long-term catheterizations include use of tissue ingrowth cuffs, generally made of a fabric such as Dacron® or the like. Such fabric cuffs are positioned around the proximal portions of catheters which are to be positioned in a subcutaneous area for securement. The fabric grows into the surrounding tissue and the catheter is fixed and can be left in that position for a significant length of time. Such cuffs generally require tunnelization of subcutaneous tissue, which involves first creating a subcutaneous tunnel or similar opening several centimeters adjacent to and caudal to the insertion site of the catheter and then passing the catheter through the tunnel. Tunnelization is generally used in combination with catheters having a fabric cuff as described above, or other retaining devices or fittings for subcutaneous securement. Subcutaneous tunnels and stabilizing devices are typically used, for example, with long-term catheterization using Tesio catheters.

A self-securing multiple catheter assembly is also available and is known as the Schon catheter available from Medical Components, Inc. of Harleysville, Pennsylvania. The Schon catheter includes two single lumen catheters joined in only one location by a polymer-based retaining sleeve. The portions of the catheter distal to the retaining sleeve are positioned in a vessel such as an internal jugular vein, and the portions of the catheters proximal to the retaining sleeve are positioned in two separate subcutaneous

3 tunnels formed at an acute angle with respect to each other. The retaining sleeve is positioned on the catheter such that when the catheter has been inserted in the vessel and the proximal portions have been positioned in the subcutaneous tunnels, the retaining sleeve is implanted in the subcutaneous tissue between the vessel and the entrance points into the two subcutaneous tunnels. As such, the retaining sleeve acts as an internal anchoring device such that if force is placed on the proximal ends of the catheters extending from the body, the retaining sleeve prevents the catheter from being pulled out of the body through the subcutaneous tunnels. The proximal portions of the catheters can further be provided with fabric stabilizing cuffs if desired.

While fabric cuffs and other tunnellized securement techniques are suitable for use in most chronic procedures, they may present difficulties for use in acute procedures. The tunnelization procedure for chronic Tesio placement can be time consuming as it requires undertaking two separate tunnelling procedures, one for each catheter. In acute procedures, time is of the essence. Thus, there is a need in the art for a multiple catheter assembly that provides the advantages and benefits of Tesio catheters but which avoids time-consuming stabilization procedures as described above for use particularly in acute catheterization. The present invention fills such a need.

BRIEF SUMMARY OF THE INVENTION

The present invention includes a double catheter assembly useful for vascular access which comprises two single lumen catheters, each having an external portion and an implantable portion along their respective lengths. The assembly also comprises a stabilizer disk having opposed surfaces through which each of the two catheters pass at a transition point along the catheter length between the external portion and the implantable portion, the catheters passing through and being secured to the disk in a juxtaposed relationship with each other at a centrally located portion of the disk. Each of the catheters has a permanent bend in the external portion of each of the catheters proximate to the stabilizer disk. The bend has a sufficient radius of curvature for avoiding constriction of the catheter lumen and is at an angle for facilitating placement and routing of the external portions of the catheters remote from the bend next to a patient's skin during a catheterization.

In one embodiment, the double catheter assembly useful for vascular access comprises two single lumen catheters and a stabilizing disk. Each of the single lumen catheters has an external portion and an implantable portion along its respective length. The stabilizer disk has opposed planar surfaces through which each of the two catheters is passed at a transition point along the catheter length between the external portion and the implantable portion. The catheter is passed through and is secured to the disk in a juxtaposed relationship with each other at a centrally located portion of the disk in a substantially perpendicular orientation to the disk planar surfaces. Each of the catheters has a permanent right angle bend in the external portion of each of the catheters proximate to the stabilizer disk. The bend has sufficient radius of curvature for avoiding constriction of the catheter lumen.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings, like numerals are used to indicate like elements throughout. In the drawings:

FIG. 1 is a perspective view of a preferred embodiment of a double catheter assembly according to the present invention;

FIG. 2 is an enlarged plan view of the stabilizer disk in the catheter assembly of FIG. 1;

FIG. 3 is an enlarged cross-sectional view of the stabilizer disk shown in FIG. 2 taken along line 3—3; and FIG. 4 is an enlarged plan view of a section of the implantable portion of the first and second catheters within the assembly of FIG. 1;

DETAILED DESCRIPTION OF THE INVENTION

Figure 5:
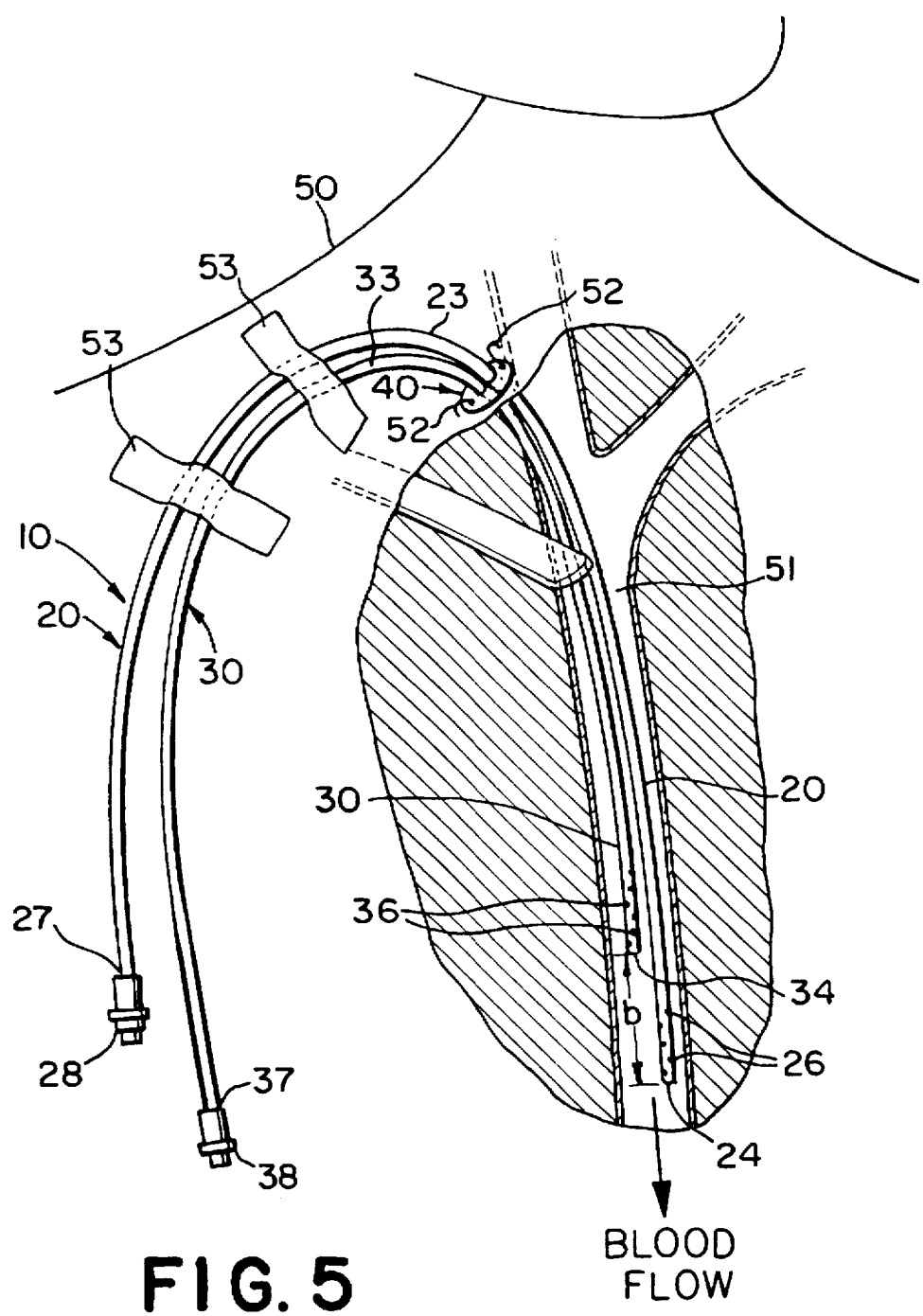
FIG. 5 is partially broken-away diagrammatic view of a preferred embodiment of a catheter assembly according to the present invention secured in position after insertion into a patient's internal jugular vein.

Certain terminology is used in the following description for convenience only and is not limiting. The words "right," "left," "lower" and "upper" designate directions in the drawings to which reference is made. The words "external" and "implantable" refer to regions along the length of the catheters that correspond to the respective portions that ordinarily are outside the patient's body and inside the patient's body when the device is used in a catheterization. "Distal" and "proximal" refer to directions toward and away from respectively, the end of the catheter which is inserted in an area to be catheterized. The terminology includes the words above specifically mentioned, derivatives thereof, and words of similar import.

Referring now to the drawings in detail, there is shown in FIGS. 1 through 5 a preferred embodiment of a double catheter assembly or device, generally indicated as 10. As shown in FIG. 1, the principal components of the double catheter assembly 10 are two independent single lumen catheters 20, 30 and a stabilizer disk 40 that secures the two catheters 20, 30 together and serves to stabilize the catheter assembly 10 at the insertion point on a patient's body when the assembly is used in a catheterization, typically as shown in FIG. 5. The catheters 20, 30 of this invention are also characterized by having permanent bends 23, 33 in the respective external portions 21, 31 of the catheters 20, 30 that are adjacent to the stabilizer disk 40 and that lie outside the patient's body when the catheter assembly 10 is used in a catheterization.

These and other aspects of the invention will now be described in more detail. As shown in FIG. 1, the preferred assembly 10 according to the present invention is a dual catheter assembly which includes a first catheter 20, a second catheter 30, and a stabilizer disk 40. It will be understood from the disclosure, that additional catheters (not shown), including triple and other multiple lumen catheter assemblies, which have implantable portions for inserting into the area to be catheterized in a manner as shown in FIG. 5, could also be positioned within the stabilizer disk such that external portions of such catheters are outside of the body and the stabilizer disk functions to secure all of the catheters in position at the insertion point on the body. Such an assembly is contemplated as within the scope of the present invention as an alternative assembly adaptable for other related applications. However, for clarity and convenience, the present invention will be described below in the preferred assembly embodiment which includes an improved Tesio system assembly 10 having two single lumen catheters 20, 30 and a stabilizer disk 40 as shown in FIGS. 1–5.

The double catheter assembly 10 can be adapted for use in various applications in which bodily fluids, medicaments or other solutions are introduced and removed from the body such as perfusion, infusion, plasmapheresis, hemodialysis, chemotherapy, and the like. For the purposes of describing the preferred embodiment of the present invention, the double catheter assembly 10 will be described with respect to the preferred application of a hemodialysis catheterization, such as the internal jugular vein catheterization as depicted (in part) in FIG. 5. However, it should be understood by one skilled in the art based on this disclosure, that the assembly 10 can be configured and adapted, by increasing or decreasing the catheter size and/or number, such that the assembly 10 can be beneficially used for other medical applications in which fluids are introduced and/or removed from the body.

The first catheter 20 and the second catheter 30, as well as the stabilizer disk 40, are preferably made of a biocompatible polymeric material, for example, an elastomer. Highly preferred polymeric materials include medical grade polyurethanes and silicone rubbers.

Suitable biocompatible polymeric materials include, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheters 20, 30, it is preferred that the polymeric material includes a polyurethane or a polyolefin polymeric material.

Suitable biocompatible elastomers for use in forming the catheters 20, 30 include medical grade silicone rubbers, polyvinyl chloride elastomers, polyolefin homopolymeric and copolymeric elastomers, urethane-based elastomers, and natural rubber or other synthetic rubbers.

The catheters 20, 30 and stabilizer disk 40 are preferably made of a soft flexible material that is durable and easily conformable to the shape of the target area to be catheterized as described below. Catheters 20, 30 that are made of a soft flexible material are highly preferred since they are less traumatic for vascular access. A highly preferred soft flexible material is polyurethane, which can be fabricated into relatively thin walled catheters with high wall strength.

As best shown in FIG. 1, the first catheter 20 is in the shape of an elongated tube having an external portion 21, and an implantable portion 22. The external portion 21 is the section of the catheter 20 which remains outside of the body during catheterization. The implantable portion 22 is the section of the catheter 20 which is introduced into the body during catheterization. Depending on the intended medical application and type of catheterization, the length of the external and implantable portions 21, 22 of the catheter 20 may vary. A representative length for the implantable portion (measured from the stabilizer disk 40 to the end or tip of the catheter) may typically range between about 15 cm for subclavian or internal jugular vein use to about 22 cm for femoral vein catheterization. The size also varies within a given type of catheterization application depending upon patient size.

The second catheter 30 is generally similar to the first catheter 20 with respect to the characteristics and features just described. The second catheter 30 has an external portion 31 and an implantable portion 32, as shown in FIG. 1. However, it should be recognized that, as shown in FIGS. 1, 4 and 5, the respective lengths of the implantable portions 22, 32 of the catheters 20, 30 are preferably different, for catheterization performance reasons as described below.

The two catheters 20, 30 are preferably two single lumen catheters that are separate, independent catheters whose respective external length portions 21, 31 and implantable length portions 22, 32 are not conjoined along their lengthwise direction. The two catheters 20, 30 are, however, in a juxtaposed relationship at the point where they pass through the stabilizer disk 40 and may optionally be conjoined at that point.

The preferred embodiment of the double catheter assembly 10 shown in FIGS. 1–5 is useful in hemodialysis catheterizations and desirably has a first catheter 20 with an implantable portion 22 length of about 18 cm (7.1 in) and a second catheter 30 with an implantable portion 32 length of about 15 cm (5.9 in). These lengths also vary with a given use and with patient sizes. The implantable portion length is the distance from the stabilizer disk 40 to the end or tip of the catheter portion that is placed or inserted inside of the patient's body during a catheterization.

The catheters 20, 30 are preferably made of soft flexible silicone elastomer having a hardness of about 80-A on a Shore durometer scale and capable of withstanding sterilization by autoclaving. The catheters 20, 30 may also be radiopaque, for example, by addition of inorganic salts such as barium sulfate to the polymeric material.

As is best shown in FIG. 3, the preferred double catheter assembly 10 of this invention contains catheter tubes 20, 30 that are hollow, elongated cylinders. An exemplary catheter assembly 10 may have catheters 20, 30 which each have an outside diameter (OD) of about 0.318 cm (0.125 in) and a single lumen 25, 35 concentrically located within the tube and having an inside diameter (ID) of 0.203 cm (0.080 in).

As shown in FIG. 1, the double catheter assembly 10 of this invention is further characterized by having permanent bends 23, 33 in the external portions 21, 31 of each of the catheters 20, 30. The respective bends 23, 33 in catheters 20, 30 have a radius of curvature sufficiently large to avoid constriction of the lumens 25, 35 (see FIG. 3) in the catheters, in a manner that would appreciably restrict fluid flow through the lumens. The bends 23, 33 may be characterized as being a rounded or "soft" bend, rather than an abrupt or "hard" bend in the catheter. A radius of curvature of at least about 2.54 cm (1 in) would be satisfactory, for a preferred catheter tube having an OD of about 0.318 cm (0.125 in) and an ID of 0.203 cm (0.080 in). However, the radius of curvature could be varied for different diameter tubings. The bends 23, 33 serve to promote patient compliance by minimizing discomfort or annoyance with the protruding external portion of the catheter when the double catheter assembly 10 is used in a catheterization. The bends 23, 33 facilitate placement of the external portions 21, 31 of catheters 20, 30, exiting from the point on the patient's body where the catheters are inserted for catheterization (insertion point), by allowing such external portions remote from the bend to be routed parallel to the surface of the patient's body, preferably next to the skin, near the insertion point.

In a preferred embodiment of a double catheter assembly 10 as shown in FIGS. 1–3 and 5 where the catheters 20, 30 pass through the stabilizer disk 40 in a substantially perpendicular orientation with respect to the planar disk surfaces 43, 44. The permanent bends 23, 33 in the external portions are preferably right angle bends. Such permanent right angle bends 23, 33 in each of the catheters 20, 30 are approximately 90°, but it will be appreciated from the disclosure herein that the angle may be somewhat more or less, for example, ±20°, than a right angle bend without significantly adversely affecting the intended function as described above.

In an alternative embodiment of the catheter assembly 10 (not shown), the catheters 20, 30 pass through the stabilizer disk 40 at an orientation with respect to the surfaces 43, 44 of the disk other than substantially perpendicular. In such a case, the angle of deviation from perpendicular and the angle of permanent bends 23, 33 should preferably add up to approximately 90°, that is, a right angle. For example, if the catheter 20, 30 orientation in the stabilizer disk is about 40° off of perpendicular, then the bends 23, 33 should each be at about a 50° angle.

The bends 23, 33 are preferably "pre-bent" and may be formed by bending the catheter tubing into the appropriate angle with the application of heat, for example, using heated air or other heated fluid, for example, boiling water, or a heat lamp and then cooling the catheter while maintaining the desired bend, to allow the polymeric material to permanently set at the desired angle. The desired bend angle in the catheter tube may be maintained during this heating and cooling "setting" procedure by an internal wire form or other mandrel passed through the lumen or by external braces or forms used to hold the catheter tubing in place.

A stabilizer disk 40 is located on the catheter assembly 10 at the transition point along each of the catheters 20, 30 between the external portions 21, 31 of the catheters and the implanted portions 22, 32 of the catheters. The stabilizer disk 40 in the catheter assembly 10 serves several functions, which make the catheter assembly particularly simple to use. The stabilizer disk 40 maintains the two catheters 20, 30 in the proper juxtaposed position, being aligned in a parallel proximate relationship with each other, at a central location in the disk 40. The catheter orientation is preferably in a substantially vertical, more preferably substantially perpendicular, orientation with respect to the planar disk surfaces 43, 44 as best shown in FIG. 2. Referring now to FIG. 5 as illustrative, the stabilizer disk 40 also serves as an anchoring means for stabilizing the catheter assembly at the insertion point on the body where the implantable portions of the two catheters enter the body. The stabilizer disk 40 also acts to protect the catheter entrance site, for example, such as an incision, from microbial contamination or entry of other foreign matter. During use of the double catheter assembly during a catheterization, the stabilizer disk 40 further provides a means for maintaining the proper implanted lengths of the two catheters 20, 30 as well as assuring the desired difference in lengths of the implantable portions 22, 32 of the two catheters.

The shape of the stabilizer disk 40 is preferably circular with opposing planar surfaces, as shown in FIGS. 1–3. However, other shapes or geometries are also feasible, for example, oval or polygonal shapes could also be used to provide the same functions, and one or both of the opposing surfaces of the disk could be other than planar, for example, the disk could be domed or hemispherical in shape on the side of the disk not normally in contact with a patient's skin during a catheterization. The term "disk" as used in this specification is not intended to limit the geometry or shape of the stabilizer disk 40 to a conventional disk shape as shown.

The overall size of the stabilizer disk 40, that is, its diameter or surface area, should be sufficiently large to prevent the disk 40 from passing through the catheter insertion point in the patient's body. The size of the stabilizer disk 40 should also be sufficient to permit the disk 40 to be securely positioned and attached at the catheter insertion point on the patient's body (typically as shown in FIG. 5), as well as to maintain and support the catheters 20, 30 in the disk 40 in the desired orientation with respect to the surfaces 43, 44 of the disk 40 (a preferred substantially perpendicular orientation of the catheter tubes being shown in FIG. 2).

The stabilizer disk 40 shown in the preferred double catheter assembly of FIGS. 1–3 and 5 is circular in cross-sectional shape, with a disk diameter of at least about 2.5 cm (0.98 in) being preferred. The thickness of the stabilizer disk 40 is not critical, as long as the thickness is sufficient to provide adequate structural integrity of the disk, for example, supporting the catheters in the desired orientation during use of the assembly in a catheterization. A uniform thickness of the stabilizer disk 40 is preferred, but other disk geometries may also be used, such as a disk with a thicker central portion and a thin peripheral edge portion. With silicone elastomers, a thickness of at least about 0.2 cm (0.08 in) is generally satisfactory. Thus, the stabilizer disk 40 typically has the appearance of a thin wafer, as shown in FIGS. 2 and 3.

Referring now to FIG. 3, the periphery of the stabilizer disk 40 preferably contains a plurality, two or more, of openings 41 that may be used to stitch or suture the stabilizer disk to the patient when the assembly is used in a catheterization, such as is shown in FIG. 5. As is best shown in FIG. 3, the stabilizer disk 40 contains four holes 41 symmetrically spaced or positioned around the perimeter of the stabilizer disk. Although round holes or eyelets are shown, the holes 41 could be in other shapes, such as slots or the like.

Other means for attaching the stabilizer disk 40 to the patient's skin may also be used, for example, a biocompatible medical grade releasable adhesive (not shown) may be applied to the planar surface 44 of the stabilizer disk 40 that is contacted with the patient's skin.

It is important to note that the stabilizer disk 40 in the double catheter assembly 10 of this invention serves as an external attachment and stabilizing means. Since it is not implanted, either partially or totally, in the body, the catheterization procedure for using the device 10 of this invention is therefore straightforward and readily adapted for use in acute catheterizations, particularly in emergency situations.

As described earlier, the stabilizer disk 40 may be made of a biocompatible material that is the same as that used to fabricate the catheters 20, 30, or it may be made of a different biocompatible material. In a preferred embodiment (not shown), the stabilizer disk 40 has its exterior surfaces made of metallic silver, which may be either a coating on the stabilizer disk or the material used to construct the disk itself.

The stabilizer disk 40 may also have medications, such as medicated ointment, applied to it, particularly on the planar surface of the disk in contact with the patient's body, to reduce the risk of infection.

The stabilizer disk 40 is positioned on the catheters 20, 30 in the catheter assembly 10 at a point which divides the catheters into respective external length portions 21, 31 and implantable length portions 22, 32. The catheters 20, 30 desirably pass through the stabilizer disk 40 in a centrally located area of the disk surfaces 43, 44, with the catheters being in a parallel and juxtaposed relationship to each other, as is shown in FIGS. 1, 2 and 3.

The first and second catheters 20, 30 are preferably positioned in a semi-permanent or permanent manner in the stabilizer disk 40. Semi-permanent positioning may be accomplished by a snug but secure frictional fit of the catheters in the holes 42, as shown in FIG. 3, in the stabilizer disk 40 through which the catheters 20, 30 pass. In the embodiment where the catheters are positioned in a semi-permanent manner, a physician, or other medical personnel, may move and position the stabilizer disk 40 along the lengths of the catheters 20, 30 prior to or after insertion of the implantable length portions of the catheters 20, 30. In a preferred embodiment of the present invention, however, the catheters 20, 30 are already permanently positioned in the stabilizer disk 40 to avoid the time, effort and judgment required for properly positioning or otherwise adjusting the catheters 20, 30 in the stabilizer disk 40.

Permanent positioning of the catheters in the stabilizer disk 40 is preferred, and this may be accomplished by use of a medical grade adhesive, by heat, molding, or by ultrasonic welding (not shown in the Figs.). Any suitable pressure or heat sensitive medical grade adhesive may be used such as, for example, Dow Corning Silicone Medical Grade Adhesive. However, other biocompatible adhesives are also acceptable. Methods for heat-molding or ultrasonically welding the exterior surfaces of the catheters 20, 30 to the stabilizer disk 40 include any suitable methods which would be known to one of ordinary skill in the art. It should be understood based on this disclosure, that other methods for permanently positioning the stabilizer disk 40 with respect to the catheters 20, 30 are contemplated.

As shown for the preferred embodiment in FIG. 3, the holes 42 or other openings in the stabilizer disk 40 are sized to fit securely around the first and second catheters 20, 30 that pass through the disk in a juxtaposed relationship with the catheters'lengthwise axes being substantially perpendicular to the two planar surfaces of the disk, as shown in FIGS. 1, 2 and 3. The holes 42 or other openings in the stabilizer disk 40 are determined in accordance with the outer diameters of the catheters 20, 30 that are positioned in the disk 40 such that a secure fit is provided, as shown in FIG. 3. Although the embodiment of the stabilizer disk 40 shown in FIG. 3 shows the circumferences of the two circular openings 42 for passage of the catheters 20, 30 being in tangential contact at one point, the holes 42 may alternatively be separate from each other, provided that the juxtaposed relationship of the catheters is substantially maintained.

Other characteristics of the catheters 20, 30 are now described in more detail. As is best shown in FIGS. 3 and 4, the first catheter 20 is a tube-like structure having a single lumen 25 that is concentrically located within the catheter.

The lumen 25 extends lengthwise along the longitudinal axis of the first catheter 20, preferably along the full length of the catheter 20. In a similar manner, the second catheter 30 has a single lumen 35. The second lumen 35 likewise extends longitudinally through the second catheter 30, preferably along the full length of the catheter 30. The lumens 25, 35 preferably each have a generally circular cross section as viewed along a plane perpendicular to the longitudinal axis of each of the catheters 20, 30. For any desired outside diameter for the catheter, the catheter tube wall thickness is desirably made as thin as possible without compromising wall strength, kinking resistance and other similar characteristics of the catheter, to maximize fluid flow rates through the lumen. While a circular cross section is preferred in order to achieve efficient fluid flow in each lumen 25, 35, other lumen cross-sectional configurations may be used without departing from the spirit of the present invention, such as for example, oval, elliptical, or kidney-bean shaped. While configurations such as semi-circular, rectangular, and the like may be used, they are not preferred as the sharper corners typically decrease flow efficiencies and increase turbulent flow within the lumens. In addition, while two lumens 25, 35 of equal cross-sectional area are preferred as shown in FIG. 3, the two lumens in the catheter assembly 10 may be of different cross-sectional areas (such as, for example, providing a smaller lumen for infusion of medication).

Referring now to FIG. 4, the implantable ends 24, 34 of the implantable portions 22, 32 of the first and second catheters 20, 30, respectively, are preferably blunt in that they are configured to lie generally in a plane which is perpendicular to the longitudinal axis of each catheter 20, 30. The lumens 25, 35, shown in FIG. 3 but not FIG. 4, at the implantable ends 24, 34 of the catheters 20, 30 are exposed to the full extent of their cross sectional area. The ends 24, 34 may alternatively be slightly rounded (not shown). The ends 24, 34 are preferably integral with the catheters as shown in the preferred embodiment and are preferably formed of a flexible material such as a soft polyurethane elastomer or silicone elastomer as described above. By configuring the implantable ends 24, 34 in a blunt design and forming the ends 24, 34 from a polymeric material such as a soft polyurethane elastomer, trauma to the area to be catheterized 12 and stenosis are minimized. It should be understood from this disclosure that while blunt ends 24, 34 are preferred for hemodialysis applications, other end configurations are possible, such as, for example, tapered or slightly pointed ends or bias cut ends which facilitate insertion or accommodate other potential applications of the double catheter assembly 10. Such tapered, slightly pointed or bias cut designs are not preferred for blood treatment applications using the double catheter assembly 10, however, as they tend to increase the risk of vessel wall trauma and stenosis.

As shown in FIG. 4, it is preferred that a first and second plurality of apertures 26, 36 be provided to the implantable ends 24, 34 of the first and second catheters 20, 30, respectively. The apertures 26, 36 preferably extend through the walls of the respective catheters 20, 30 and open into the respective lumens 25, 35 of the two catheters. The apertures 26, 36 are useful for providing more even intake and return flow of fluids through the lumens 25, 35. The apertures 26, 36 also provide alternative, additional openings in the implantable portions 32, 32 of the catheters 20, 30 such that flow may continue even if the lumen openings at the ends 24, 34 of the two catheters 20, 30 become blocked, clogged or otherwise occluded. By providing access for fluid to enter and leave the lumens 25, 35 through the apertures 26, 36, the likelihood of undesirable movement (for example, fluttering) of the catheters 20, 30 within the area being catheterized, such as an internal jugular vein 51 (shown in FIG. 5), is reduced. This stabilizing function is obtained by spacing the apertures 26, 36 in a helical arrangement around the circumference of the catheters 20, 30 near the ends 24, 34 of the implantable portions 22, 32 of the two catheters, as is shown in FIG. 4.

Referring now to FIG. 5, connectors 28, 38 may be attached to the external ends 27, 37 of the catheters 20, 30 such that the catheters may be attached to other devices such as, for example, a hemodialysis apparatus or an injection or fluid medication system. The connectors 28, 38 shown in FIG. 5 are female Luer lock adapters. Other examples of suitable connectors include quick connect fittings, ferrule connectors, threadable connectors, and the like. In addition, clamps (not shown) may also be provided on the external portions 21, 31 of the catheters 20, 30 for regulation or interruption of flow of fluid through the lumens 25, 35.

The double catheter assembly 10 with catheters 20, 30 can be used for the introduction and removal of fluids from an area to be catheterized, such as is shown in FIG. 5. In FIG. 5, the area of the body 50 to be catheterized includes the internal jugular vein 51. Other areas in which the catheter assembly 10 may be used include, for example, other blood vessels, including the femoral and subclavian veins, any abscess cavity, postoperative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly 10 may be used to remove or introduce fluids in various areas of the body 50 where a catheterization is desirably performed. The preferred double catheter assembly 10 as shown in FIG. 5 is useful for intake, or removal, of blood to be purified, medicated or otherwise treated from a blood vessel, such as the internal jugular vein 51, and introduction of purified, medicated or otherwise treated blood into the same vessel 51 as shown in FIG. 5. The blood can be purified, medicated or treated by any suitable apparatus (not shown) conventionally used for such purposes. The double catheter assembly 10 may also be used to introduce medication or other fluids such as glucose or saline solutions into the body.

The catheters 20, 30 of the double catheter assembly 10 each include an implantable portion 22, 32 respectively as shown in FIGS. 1 and 5. The implantable portions 22, 32 are configured to be placed in, or preferably inserted into, the area to be catheterized, such as a vein or other body cavity, and to remain implanted during catheterization. For example, as shown in FIG. 5, the implantable portions 22, 32 of the catheters 20, 30 are configured to have a suitable length and diameter to be useful for insertion into the internal jugular vein 51. If used for hemodialysis applications, it is particularly preferred that the end 34 of the implantable portion 32 of the second catheter 30 be proximally and longitudinally spaced from the implantable end 24 of the first catheter 20 by a sufficient distance b (shown in FIGS. 1, 4 and 5) which essentially prevents recirculation of the treated blood and untreated blood to be treated. The distance b in respective implantable lengths 22, 32 of catheters 20 and 30 is preferably about 3 centimeters; however, it should be understood by one of ordinary skill in the art based on this disclosure, that such distance b could be varied for different applications of the catheter assembly 10.

Blood is preferably drawn out of a blood vessel such as the internal jugular 51 through a lumen opening in the implantable end 24 of the first catheter 20 as shown in FIGS. 4 and 5. Preferably the lumen opening in the implantable end 24 of the first catheter 20 is at least coextensive with the circular cross-sectional area of first lumen 25 (shown in FIG. 3). Blood is returned through a lumen opening in the implantable end 34 of the second catheter 30 as shown in FIGS. 4 and 5. The lumen opening is preferably at least coextensive with the circular cross-sectional area of the second lumen 35 (shown in FIG. 3).

When the double catheter assembly 10 is used in a preferred catheterization application, that is, blood treatments such as hemodialysis, blood is preferably drawn from the implantable end 24 of the longer first catheter in the present invention. It should be understood by one of ordinary skill in the art, based on this disclosure, that the direction of flow can be reversed, in the manner of other catheter designs, such that the implantable end 24 of the longer, first catheter 20 is used for returning treated blood, or other fluid, to the area to be catheterized, such as the internal jugular vein 51.

The catheter assembly 10 of the present invention, which is preferably used with a flow direction reversed from the conventional flow pattern of prior art catheters in which the longer lumen is the return lumen, provides the benefit of being operational at higher flow rates. The treated blood is returned upstream and proximally from the area where the blood to be treated is drawn a distance of preferably about 3–4 cm. The separation distance b is preferably longer than the traditional spacing of return and intake openings of multiple lumen catheters, which is typically about 2 cm. The preferred longer distance b, in combination with the ability of the implantable portions 22, 32 to move independently in the vessel 51, help to prevent recirculation of treated blood returned upstream through the lumen and apertures in the second catheter end 34 with blood to be treated being drawn into the first catheter 20 through the lumen and apertures in the first catheter end 24.

When the catheter assembly 10 is used for hemodialysis and the area to be catheterized is the internal jugular vein 51, an insertion site (not shown) will be made in the vicinity of the clavicle; in FIG. 5, for example, the insertion site is an incision (not visible) located underneath the stabilizer disk 40. The exact location of the insertion site can be varied as determined by the physician. In placing the catheter assembly 10 in the an area to be catheterized such as an internal jugular vein 51 as shown in FIG. 5, a needle (not shown), typically an 18 gauge needle, is used to locate the vein 51 by methods used by those of ordinary skill in the art. A guide wire (not shown) is introduced through the needle into the vein 51. An incision is made at an insertion site, and a tear-away sheath assembly (preferably about 18 French in diameter) including a sheath and a dilator (not shown) is slipped into the vein 51 over the guide wire in accordance with techniques used by those of ordinary skill in the art. The guide wire and dilator are removed. The catheter assembly 10 is inserted through the sheath (not shown). Alternatively, the sheath may also function as a dilator. The implantable portions 22, 32 of the catheters 20, 30 of the double catheter assembly 10 are introduced into the vein 51 through the sheath until the stabilizer disk 40 is positioned just outside the incision leading to the vein 51. When the stabilizer disk 40 reaches the top of the sheath, the sheath is peeled away leaving the implantable portions 22, 32 of the catheters 20, 30 situated in the vein 51.

When the implantable portions 22, 32 of the catheters are completely inserted below the surface of the skin and catheters 20, 30 are properly positioned in the vein 51, the stabilizer disk 40 is sutured or stitched to the skin or epidermis surrounding the incision point using holes 41 in the stabilizer disk as attachment points for the sutures 52. Prior to attaching the stabilizer disk 40 to the patient's body, the incision site may optionally be closed around the catheters 20, 30 leading into the vein 51. When the stabilizer disk 40 is properly positioned and secured with sutures 52 to the patient as described above, the stabilizer disk covers the incision point and provides protection against infection from microbial contamination, including pericannular microbial migration, and entry of other foreign matter. The stabilizer disk 40 thus secures the catheter assembly 10 in place, and the assembly 10 cannot be pulled from the area of catheterization due to the sutures 52 that retain the externally attached stabilizer disk 40 in a fixed position on the patient's body 50 at the incision point. As shown in FIG. 5, the stabilizer disk 40 is positioned on the patient's skin, outside of the body 50, and thus avoids the need for subcutaneous attachment means often used in prior art catheterizations.

The external length portions 21, 31 of catheters 20, 30 are secured flat on the patient's body 51 with tape strips 53, as shown in FIG. 5. The right angle bends 23, 33 in the external portions 21, 31 of the catheters 20, 30 facilitate the taping of the two external portions 21, 31 flat against the patient's body, as shown in FIG. 5, notwithstanding the fact that the two catheters 20, 30 exit from the stabilizer disk 40 in a substantially perpendicular direction. The respective ends 27, 37 of the external portions 21, 31 of catheters 20, 30 are fitted with female Luer connectors 28, 38, as shown in FIG. 5. These connectors 28, 38 facilitate connection of the double catheter assembly 10 to conventional catheterization treatment apparatus (not shown), such as a hemodialysis apparatus, so that treatment of the patient may be carried out in a conventional manner. The design of the double catheter assembly 10 of this invention and its use in catheterizations as described above make this device particularly well suited for use in acute catheterization situations, typically emergency medical treatments that require catheterization of the patient in need in a relatively short time frame.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A double catheter assembly useful for vascular access which comprises:

two single lumen catheters, each having an external portion and an implantable portion along their respective lengths;

a stabilizer disk having opposed surfaces through which each of the two catheters pass at a transition point along the catheter lengths between the external portions and the implantable portions, said transition point being located for externally attaching said disk to a patient's skin;

said catheters passing through holes formed transversely through said disk and being secured within said holes of the disk in a juxtaposed and parallel relationship with each other at a centrally located portion of the disk; and each of said catheters having a heat set bend in the external portion of each of said catheters proximate to the stabilizer disk, said bends having sufficient radius of curvature for avoiding constriction of the catheter lumens and being at an angle for facilitating placement and routing of the external portions of the catheters remote from the bends next to a patient's skin during a catheterization.

2. The double catheter assembly according to claim 1, wherein the catheters pass through and are secured within said holes of the disk in a substantially vertical orientation to the disk surfaces.

3. The double catheter assembly according to claim 2, wherein the bend in the external portion of each of said catheters is substantially a right angle bend.

4. The double catheter assembly according to claim 1, wherein the double catheter assembly is made of a soft flexible material.

5. The double catheter assembly according to claim 4, wherein the material is an elastomeric polymer.

6. The double catheter assembly according to claim 4, wherein the material is polyurethane or silicone rubber.

7. The double catheter assembly according to claim 1, wherein the single lumen catheters are independent, separate catheters that are not conjoined along their lengths.

8. The double catheter assembly according to claim 1, wherein the respective implantable portions of the two catheters are of different lengths.

9. The double catheter assembly according to claim 1, wherein the stabilizer disk contains a plurality of holes adjacent to the perimeter of the stabilizer disk.

10. The double catheter assembly of claim 1, wherein the external surfaces of the stabilizer disk are metallic silver.

11. The double catheter assembly according to claim 1, further comprising connectors located at the ends of the external portions of the catheters remote from the stabilizer disk.

12. The double catheter assembly according to claim 1, wherein the catheters are permanently secured within the holes of the disk.

13. A double catheter assembly useful for vascular access which comprises:

two single lumen catheters, each having an external portion and an implantable portion along their respective lengths;

a stabilizer disk having opposed planar surfaces through which each of the two catheters pass at a transition point along the catheter lengths between the external portions and the implantable portions, said transition point being located for externally attaching said disk to a patient's skin;

said catheters passing through holes formed transversely through said disk and being secured within said holes of the disk in a juxtaposed and parallel relationship with each other at a centrally located portion of the disk in a substantially perpendicular orientation to the disk planar surfaces; and each of said catheters having a heat set right angle bend in the external portion of each of said catheters proximate to the stabilizer disk, said bends having sufficient radius of curvature for avoiding constriction of the catheter lumens.

14. The double catheter assembly according to claim 13, wherein the catheters are permanently secured within the holes of the disk.

15. A double catheter assembly useful for acute catheterization procedures which comprises:

two single lumen catheters, each having an external portion and an implantable portion along their respective lengths;

a stabilizer disk having opposed planar surfaces through which each of the two catheters pass at a transition point along the catheter lengths between the external portions and the implantable portions, said transition point being located for externally attaching said disk to a patient's skin;

said catheters passing through holes formed transversely through said disk in a substantially juxtaposed and parallel relationship with each other at a centrally located portion of the disk; and each of said catheters having a heat set bend in the external portion of each of said catheters proximate to the stabilizer disk, said bends having sufficient radius of curvature for avoiding constriction of the catheter lumens and being at an angle for facilitating placement and routing of the external portions of the catheters remote from the bends next to a patient's skin during a catheterization.

16. The double catheter assembly according to claim 15, wherein the catheters are juxtaposed and permanently secured within the holes of the disk.

* * * * *